United States Patent [19]

Kurisaki et al.

[11] Patent Number: 5,024,831
[45] Date of Patent: Jun. 18, 1991

[54] POWDERY COSMETIC CONTAINING CELLULOSE POWDER IMPREGNATED WITH MOISTURIZING POLYMER

[75] Inventors: Hideo Kurisaki; Masahiko Nishikawa, both of Kumamoto, Japan

[73] Assignee: Chisso Corporation, Japan

[21] Appl. No.: 431,249

[22] Filed: Nov. 3, 1989

[51] Int. Cl.$^5$ ............................................. A61K 7/02
[52] U.S. Cl. ........................................ 424/69; 424/63; 424/489; 424/78
[58] Field of Search ................... 424/69, 63, 401, 489, 424/493, 497, 78

[56] References Cited

FOREIGN PATENT DOCUMENTS 61-100514  5/1986  Japan ...................................... 424/69

OTHER PUBLICATIONS

Patent Abstracts of Japan, vol. 11, No. 167, May 28, 1987, p. 125, Abstracting Japanese Published Patent Application 62-410.
Patent Abstracts of Japan, vol. 11, No. 85, Mar. 14, 1987, p. 163 Describes Japanese Published Patent Application No. 61-241337.

*Primary Examiner*—Thurman Page
*Assistant Examiner*—Susan S. Rucker
*Attorney, Agent, or Firm*—Leydig, Voit & Mayer

[57] ABSTRACT

The present invention provides a powdery cosmetic which is excellent in spreadability and adhesion, free from standing-out of powder after application to the skin, free from a dry and loose sensation and has characteristics necessary for powdery cosmetic.

The powdery cosmetic of the present invention comprises a porous spherical cellulose powder incorporated therein in an amount of 0.1 to 50% by weight based on the whole amount of the powdery cosmetic. The porous spherical cellulose powder has an average particle diameter of at least 3 μm and coated, impregnated, or chemically linked with at least one high molecular substance retentive of moisture.

11 Claims, No Drawings

POWDERY COSMETIC CONTAINING CELLULOSE POWDER IMPREGNATED WITH MOISTURIZING POLYMER

BACKGROUND OF THE INVENTION

1. Field of the Invention

The present invention relates to a powdery cosmetic. More particularly, the present invention is concerned with a powdery cosmetic comprising a spherical cellulose powder coated, impregnated, or chemically linked with a high molecular substance retentive of moisture in the system.

2. Description of the Prior Art

The term "powdery cosmetic" is intended to mean a powdery cosmetic in a loose state or a pressed state prepared by mixing as a main component a powder mainly composed of a constitutional pigment, such as talc, mica, titanium dioxide, or polymer powder, and optionally an inorganic pigment, such as iron oxide, or an organic pigment, with a suitable amount of an oil as an adhesive or a binder, such as a hydrocarbon or ester oil, and if necessary pressing the mixture by compression molding.

With respect to the feeling on application of a powdery cosmetic, excellent spreadability, adhesion and finish have been required in the art.

Various spherical particles, surfactants, humectants, etc. have hitherto been incorporated in powdery cosmetics for the purpose of improving their feeling on application to the skin.

Specifically, a spherical synthetic resin powder, such as spherical nylon, spherical polyethylene or spherical polystyrene, has been used in the art in order to improve the spreadability and in recent years spherical cellulose powder has been used because it is possible to improve the adhesion to the skin. However, synthetic resin powder agglomerates due to a large charging property, which unfavorably causes the power to stand-out after application to the skin. The spherical cellulose powder has no cohesiveness but absorbs the moisture present on the surface of the skin, which brings about an overly dry and loose sensation to the skin, so that no satisfactory finish can be attained. Further, swelling and shrinkage of cellulose occur due to the moisture in the air, and this causes cracking during or after shaping. This made it impossible to incorporate the cellulose powder in large amounts.

SUMMARY OF THE INVENTION

An object of the present invention is to provide a powdery cosmetic having a combination of excellent spreadability and adhesion, freedom from both the occurrence of standing-out of the powder after application to the skin and the feeling of being over dry and loose with other characteristics necessary for a powdery cosmetic.

The present invention relates to a powdery cosmetic comprising a spherical cellulose powder coated, impregnated, or chemically linked with at least one high molecular weight moisture retaining substance.

The spherical cellulose powder is preferably a porous spherical cellulose powder having an average particle diameter of 3 to 50 μm and a maximum particle diameter of 100 μm.

The high molecular weight moisture retaining substance is preferably one member or a mixture of two or more members selected from the group consisting of hyaluronic acid, chondroitin sulfuric acid, collagen, collagen hydrolysate, elastin, elastin hydrolysate, fibronectin and salts, and derivatives of the aforementioned.

The amount of incorporation of the spherical cellulose particle coated, impregnated, or chemically linked with the high molecular weight moisture retaining substance is preferably 0.1 to 50% by weight based on the whole amount of the powdery cosmetic.

DETAILED DESCRIPTION OF THE INVENTION

The present invention relates to a powdery cosmetic comprising a spherical cellulose powder coated, impregnated, or chemically linked with a high molecular weight moisture retaining substance.

It is preferred that the spherical cellulose powder used in the present invention have an average particle diameter of 3 to 50 μm and a maximum particle diameter of 100 μm or less. When the average particle diameter is less than 3 μm, no sufficient spreading effect can be attained. On the other hand, when the average particle diameter exceeds 50 μm or the maximum particle diameter exceeds 100 μm, the cellulose powder is harsh to the touch when the cosmetic is applied to the skin.

When the spherical cellulose powder is non-porous, the amount of retention of the high molecular weight moisture retaining substance is small. Therefore, porous spherical cellulose is preferred.

In the present invention, any type of spherical cellulose may be used as far as it has the above-described properties. Examples of the spherical cellulose which may be used in the present invention include those prepared by methods described in, e.g., Japanese Patent Application Laid-Open Nos. 44312/1980, 7759/1978, 38801/1982, and 241337/1986.

the terms "high molecular weight substance retentive of moisture" or "high molecular weight moisture retaining substance" or like terms are intended to mean a substance which changes the oil absorption characteristics and water absorption characteristices inherent in the powder through coating, impregnation or chemical linking of the surface and inside of the porous spherical cellulose powder with the high molecular weight substance, thereby attaining novel functional characteristics which have not been attained in the prior art. Therefore, the high molecular weight moisture retentive substance is necessary to stably maintain the functional characteristics of the powder, which renders polyhydric alcohols, such as propylene glycol and glycerin, known as a low-molecular weight humectant, unsuitable for use in the present invention. Suitable examples of the high molecular weight moisture retentive substances include substances having a molecular weight of hundreds or more, such as hyaluronic acid, chondroitin sulfuric acid, collagen, collagen hydrolysate, elastin, elastin hydrolysate, fibronectin, their salts, and their derivatives. They may be used alone or in the form of a mixture of two or more of them.

The above-described high molecular weight moisture retaining substance may be used in the present invention even when they are those extracted from the organism, newly synthesized or prepared by biological techniques.

The porous spherical cellulose powder may be coated, impregnated, or chemically linked with the above-described high molecular weight moisture retentive substance, e.g., by any of the following methods as far as the functional characteristics of the cellulose can be maintained: a method which comprises immersing, with stirring, a porous spherical cellulose powder in a solution containing a high molecular weight moisture retentive substance dissolved therein and drying the solution; a hybridization method which comprises mechanically mixing a high molecular weight moisture retentive powder with a porous spherical cellulose powder in a certain proportion to coat the surface of the cellulose or force the high molecular weight moisture retentive powder into pores of the cellulose; and a method wherein a high molecular weight moisture retentive substance is chemically bonded to the porous spherical cellulose powder through covalent or ionic bond by taking advantage of OH groups of the cellulose.

The amount of incorporation of the above-described spherical cellulose is preferably 0.1 to 50% by weight based on the whole amount of the powdery cosmetic. When the amount of incorporation is less than 0.1% by weight, the adhesion to the skin is often unsatisfactory, while the amount exceeds 50% by weight, the cosmetic is so smooth that the adhesion to the skin often becomes poor.

The powder and oil used in the present invention will now be described.

Examples of the constitutional pigment constituting the major part of the powder used in the present invention include, beside the spherical cellulose powder subjected to coating or the like with the above-described high molecular weight moisture retentive substance, constitutional pigments commonly used in cosmetics. Examples of the constitutional pigments commonly used in cosmetics include zinc white, titanium dioxide, talc, mica, clay, and kaolin, and in addition to one or two or more of them, inorganic pigments, such as iron oxide and ultramarine blue, and organic pigments may be used according to need.

Oils generally used in cosmetics may be used as the oil used in the present invention, and one or two or more of them may be arbitrarily used according to the purpose of addition thereof. Examples of the oil include higher alcohols such as cetyl alcohol and stearyl alcohol; higher fatty acids such as stearic acid and behenic acid; solid paraffin; waxes such as microcrystalline wax, polyethylene wax, candelilla wax, beeswax, hydrogenated castor oil, carnauba wax and bark wax; vegetable and animal oils such as olive oil, jojoba oil, castor oil and lanolin; mineral oils such as liquid paraffin and vaseline; and synthetic oils such as trimethylolpropane triisostearate, isopropyl myristate, glycerol tri-2-ethylhexanoate, pentaerythritol tetra-2-ethylhexanoate and silicone oil.

The amount of incorporation of the powder containing the constitutional pigment is usually 30 to 99.5% by weight based on the whole amount of the powdery cosmetic, while the amount of incorporation of the oil is usually 0.5 to 70% by weight based on the whole amount of the powdery cosmetic.

The powdery cosmetic of the present invention may be mixed with, besides the spherical cellulose powder subjected to coating or the like with the above-described high molecular weight substance retentive of moisture, the constitutional pigment optionally containing a pigment and the oil, other components commonly incorporated in a powdery cosmetic, such as surfactants, perfumes, antiseptics, mildewproofing agent, antioxidants and ultraviolet absorbers according to the purpose of addition. It is a matter of course that spherical powder other than the above-described spherical cellulose powder, e.g., spherical synthetic resin powder, also may be incorporated in such an amount as will not spoil the effect of the present invention.

The powdery cosmetic of the present invention is excellent in spreadability and adhesion, free from standing-out of the powder after application to the skin, and free from a dry and loose sensation, which gives excellent finish as a whole.

EXAMPLES

The present invention will now be described in more detail by way of test examples and working examples. However, the present invention is not limited to these only.

EXAMPLE 1

| | | |
|---|---|---|
| (1) | Spherical cellulose powder (Celluloflow-C-25 ®; a product of Chisso Corp.) | 20.0% by weight |
| (2) | Sodium hyaluronate (CHA Htype ®; a product of Chisso Corp.) | 1.0% by weight |
| (3) | Mica | 46.58% by weight |
| (4) | Talc | 10.0% by weight |
| (5) | Titanium dioxide | 7.0% by weight |
| (6) | Iron oxide (red, black, yellow) | 3.5% by weight |
| (7) | Lanolin | 5.0% by weight |
| (8) | Liquid paraffin | 5.0% by weight |
| (9) | Sorbitan sesquioleate | 1.0% by weight |
| (10) | Ethylparaben | 0.4% by weight |
| (11) | Butylhydroxyanisole | 0.02% by weight |
| (12) | Perfume | 0.5% by weight |

With respect to components (1) and (2), sodium hyaluronate was forced into pores of the spherical cellulose powder by means of a hybridization system (NHS) (a product of Nara Machinery Co., Ltd.), and mixed with components (3) to (6) in a Henschel mixer. Separately, components (7) to (12) were heated at 80° C. to dissolve them in each other, sprayed upon the above-described components (1) to (6), and put in a Henschel mixer for mixing. The mixture was ground with an atomizer and subjected to sifting and compression molding to form a pressed foundation within a cavity of a cosmetic vessel.

COMPARATIVE EXAMPLE 1

A pressed foundation was prepared in the same manner as that of Example 1, except that a spherical nylon powder (average particle diameter: 5 μm) and propylene glycol were used instead of a spherical cellulose powder and sodium hyaluronate, respectively.

EXAMPLE 2

| | | |
|---|---|---|
| (1) | Cellulose bead (bead passed through 270 mesh sieve) prepared in the same method as that described in Example 3 of Japanese Patent Application Laid-Open No. 44312/1980 | 3.0% by weight |
| (2) | Fibronectin | 1.0% by weight |
| (3) | Mica | 25.0% by weight |
| (4) | Talc | 57.95% by weight |
| (5) | Red 226 | 0.72% by weight |
| (6) | Iron oxide (red, yellow, black) | 1.62% by weight |
| (7) | Ultramarine blue | 0.69% by weight |
| (8) | Lanolin | 3.4% by weight |
| (9) | Liquid paraffin | 3.4% by weight |
| (10) | Sorbitan sesquioleate | 0.8% by weight |
| (11) | Propylparaben | 0.2% by weight |
| (12) | Butylhydroxytoluene | 0.02% by weight |

| | |
|---|---|
| -continued | |
| (13) Perfume | 0.2% by weight |

Component (1) was put in five-fold amount of 200 mM sodium periodate (NaIO$_4$) and gently shaken with stirring at 30° C. for 30 min. The mixture was subjected to suction filtration and well washed with water to prepare a formyl cellulose bead. A ten-fold amount of 5 mM Tris buffer solution and component (2) were added to the formyl cellulose bead, and the mixture was gently shaken with stirring at 5° C. for 5 hr. Then, the mixture was subjected to suction filtration, lightly washed with water, and dried with a rotary evaporator to prepare a fibronectin-bonded cellulose bead.

The fibronectin-bonded cellulose bead and components (3) to (13) were used to prepare rouge according to the method described in Example 1.

COMPARATIVE EXAMPLE 2

Rouge was prepared in the same manner as that of Example 2, except that a spherical nylon powder and polyethylene glycol (molecular weight: 3300) were used instead of cellulose bead and fibronectin, respectively.

TEST EXAMPLE

Foundations prepared in Example 1 and Comparative Example 1 were evaluated by an actual application test. In the actual application test, differences in feeling in applications of the compositions of Example 1 and Comparative Example 1 were confirmed by 20 special women panelists as subjects. The results are shown in Table 1. As can be seen from Table 1, the powdery cosmetic of the present invention was an excellent powdery cosmetic having excellent adhesion and free from the feeling of over dry and loose.

TABLE 1

| | Number of panelists who regarded Ex. 1 as being superior | Number of panelists who regared Comp. Ex. 1 as being superior | Number of panelists who regarded Ex. 1 as having the same performance as Comp. Ex. 1 |
|---|---|---|---|
| spreadability | 10 | 5 | 5 |
| freedom from standing-out of powder | 15 | 0 | 5 |
| adhesion | 11 | 5 | 4 |
| freedom from feeling of over dry | 17 | 0 | 3 |
| freedom from feeling of loose | 17 | 0 | 3 |
| finish as a whole | 18 | 0 | 2 |

Rouges prepared in Example 2 and Comparative Example 2 were evaluated in the same manner as that of Example 1 and Comparative Example 1. As a result, it was found that the rouge prepared in Example 2 was an excellent powdery cosmetic which was excellent in the adhesion and free from standing-out of powder and gave moist finish to the skin.

What is claimed is:

1. A powdery cosmetic comprising:
a spherical cellulose powder having an average particle diameter of at least 3 μm and present in an amount of 0.1 to 50% by weight based on the total weight of powdery cosmetic, said spherical cellulose powder coated, impregnated, or chemically linked with at least one high molecular weight moisture retentive substance selected from the group consisting of hyaluronic acid, chondroitin sulfuric acid, collagen, collagen hydrolyzate, elastin, elastin hydrolyzate, fibronectin and salts and derivatives of the aforementioned.

2. A powdery cosmetic according to claim 1 wherein said spherical cellulose powder comprises a porous cellulose powder.

3. A powdery cosmetic according to claim 1 wherein said spherical cellulose powder has an average particle diameter of no more than 50 μm.

4. A powdery cosmetic according to claim 1 wherein said spherical cellulose powder has a maximum particle diameter of 100 μm.

5. A powdery cosmetic according to claim 1 wherein said high molecular weight moisture retentive substance comprises hyaluronic acid.

6. A powdery cosmetic according to claim 1 wherein said powdery cosmetic further includes at least one of a constitutional pigment and an oil or wax.

7. A powdery cosmetic according to claim 6 wherein said constitutional pigment comprises at least one of zinc white, titanium dioxide, talc, mica, clay, kaolin, iron oxide, ultramarine blue, and organic pigments.

8. A powdery cosmetic according to claim 6 wherein said oil or wax comprises at least one of a higher alcohol, higher fatty acid, solid paraffin, vegetable oil, animal oil, mineral oil, synthetic oil and silicone oil.

9. A powdery cosmetic according to claim 6 wherein said oil or wax comprises at least one of cetyl alcohol, stearyl alcohol, stearic acid, behenic acid, microcrystalline wax, polyethylene wax, candelilla wax, beeswax, castor oil, hydrogenated castor oil, carnauba wax, bark wax, olive oil, jojoba oil, lanolin, liquid paraffin, vaseline, trimethylolpropane triisostearate, isopropyl myristate, glycerol tri-2-ethylhexanoate and pentaerythritol tetra-2-ethylhexanoate.

10. A powdery cosmetic comprising:
a porous, spherical cellulose powder having an average particle diameter of 3 to 50 μm and a maximum particle diameter of 100 μm, said porous spherical cellulose powder being present in an amount of 0.1 to 50% by weight based on the total weight of powdery cosmetic, and coated, impregnated, or chemically linked with at least one high molecular weight moisture retentive substance selected from the group consisting of hyaluronic acid, chondroitin sulfuric acid, collagen, collagen hydrolyzate, elastin, elastin hydrolyzate, fibronectin and salts and derivatives of the aforementioned.

11. A powdery cosmetic according to claim 10 wherein said high molecular weight moisture retentive substance comprises hyaluronic acid.

* * * * *